US00PP22560P2

(12) United States Plant Patent
Gomez Bullis

(10) Patent No.: US PP22,560 P2
(45) Date of Patent: Mar. 6, 2012

(54) ***NEOREGELIA* PLANT NAMED 'SIBELLA'**

(50) Latin Name: ***Neoregelia concentrica*×*Neoregelia 'Takamura Princeps'***
Varietal Denomination: Sibella

(75) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 11 days.

(21) Appl. No.: 12/806,816

(22) Filed: Aug. 21, 2010

(51) Int. Cl.
*A01H 5/00* (2006.01)

(52) U.S. Cl. ..... Plt./370

(58) Field of Classification Search ..... Plt./370
See application file for complete search history.

*Primary Examiner* — June Hwu

(74) *Attorney, Agent, or Firm* — C. A. Whealy

(57) ABSTRACT

A new and distinct cultivar of *Neoregelia* plant named 'Sibella', characterized by its upright and outwardly arching growth habit; broad glossy light green-colored lower leaves; broad glossy light green-colored mid-plant leaves with pink-colored apices; broad glossy pink-colored upper leaves; good interiorscape and landscape performance; and tolerance to a wide range of light levels.

1 Drawing Sheet

Botanical designation: *Neoregelia concentrica*×*Neoregelia 'Takamura Princeps'*.

Cultivar denomination: 'SIBELLA'.

BACKGROUND OF THE INVENTION

The present invention relates to a new and distinct cultivar of *Neoregelia* plant, botanically known as *Neoregelia concentrica*×*Neoregelia 'Takamura Princeps'*, and hereinafter referred to by the name 'Sibella'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia concentrica*, not patented, as the female, or seed, parent with an unnamed proprietary selection of *Neoregelia 'Takamura Princeps'*, not patented, as the male, or pollen, parent. The new *Neoregelia* plant was discovered and selected by the Inventor as a single plant within the progeny of the stated cross-pollination in a controlled greenhouse environment in Princeton, Fla. in 2002.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sibella'. These characteristics in combination distinguish 'Sibella' as a new and distinct cultivar of *Neoregelia:*

1. Upright and outwardly arching growth habit.
2. Broad glossy light green-colored lower leaves.
3. Broad glossy light green-colored mid-plant leaves with pink-colored apices.
4. Broad glossy pink-colored upper leaves.
5. Good interiorscape and landscape performance.
6. Tolerant to a wide range of light levels.

Plants of the new *Neoregelia* differ primarily from plants of the female parent selection in the following characteristics:

1. Plants of the new *Neoregelia* do not require flower bud initiation to develop upper leaf coloration whereas plants of the female parent selection require flower bud initiation to develop upper leaf coloration.
2. Upper leaves of plants of the new *Neoregelia* are pink in color whereas upper leaves of plants of the female parent selection are purple in color.

Plants of the new *Neoregelia* differ primarily from plants of the male parent selection in the following characteristics:

1. Plants of the new *Neoregelia* have broader leaves than plants of the male parent selection.
2. Plants of the new *Neoregelia* do not require flower bud initiation to develop upper leaf coloration whereas plants of the male parent selection require flower bud initiation to develop upper leaf coloration.
3. Upper leaves of plants of the new *Neoregelia* are pink in color whereas upper leaves of plants of the male parent selection are red purple in color.

Plants of the new *Neoregelia* can be compared to plants of the *Neoregelia* 'Lila', disclosed in U.S. Plant Pat. No. 11,523. In side-by-side comparisons conducted in Princeton, Fla., plants of the new *Neoregelia* and 'Lila' differed primarily in the following characteristics:

1. Plants of the new *Neoregelia* had longer and broader leaves than plants of 'Lila'.
2. Leaves of plants of the new *Neoregelia* had concentric markings whereas leaves of plants of 'Lila' did not have concentric markings.

3. Plants of the new *Neoregelia* and 'Lila' differed in leaf coloration.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Sibella' grown in a container.

The photograph at the top of the sheet is a top perspective view of a typical flowering plant of 'Sibella'.

DETAILED BOTANICAL DESCRIPTION

The aforementioned photographs and following observations, measurements and values describe flowering plants grown during the spring in 15-cm containers in a polypropylene-covered greenhouse in Princeton, Fla. under commercial *Neoregelia* production practices. During the production of the plants, day temperatures ranged from 10° C. to 32° C., night temperatures ranged from 7° C. to 32° C. and light levels averaged 3,200 foot-candles. Plants were one year old when the photographs and description were taken. In the following description, color references are made to The Royal Horticultural Society Colour Chart, 2007 Edition, except where general terms of ordinary dictionary significance are used.

Botanical classification: *Neoregelia concentrica*×*Neoregelia 'Takamura Princeps'* 'Sibella'.

Parentage:

*Female, or seed, parent.*—Unnamed proprietary selection of *Neoregelia concentrica*, not patented.

*Male, or pollen, parent.*—Unnamed proprietary selection of *Neoregelia 'Takamura Princeps'*, not patented.

Propagation:

*Type.*—By offsets.

*Time to initiate roots, summer.*—About 30 days at 30° C. to 32° C.

*Time to initiate roots, winter.*—About 45 days at 30° C. to 32° C.

*Time to produce a rooted young plant, summer.*—About three to four months at 30° C. to 32° C.

*Time to produce a rooted young plant, winter.*—About three to four months at 18° C. to 22° C.

*Root description.*—Medium in thickness, fibrous; yellow to tan in color.

*Rooting habit.*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height.*—About 18 cm.

*Plant diameter or spread.*—About 45 cm.

*Internode length.*—About 4 mm.

*Stem texture.*—Smooth, glabrous.

*Stem color.*—Close to NN155A.

Foliage description:

*Arrangement.*—Rosette, spiral phyllotaxis; simple; sessile, clasping.

*Shape.*—Oblong.

*Apex.*—Cuspidate.

*Base.*—Truncate.

*Margin.*—Serrate; spinose.

*Length.*—About 27 cm.

*Width, mid-section.*—About 7 cm.

*Width, base.*—About 9.5 cm.

*Texture.*—Smooth, glabrous; leathery; longitudinally ribbed.

*Luster.*—Glossy.

*Venation pattern.*—Parallel.

*Color.*—Lower leaves, upper surface: Close to 146A to 146C; towards the base, close to N199A; venation, close to 146A to 146C. Lower leaves, lower surface: Close to 146B to 146C; towards the base, close to 197A; venation, close to 146B to 146C. Mid-plant leaves, upper surface: Close to 146B to 146C; random splotches and concentric rings, close to 185B or 187B; towards the apex, close to 70B; venation, similar to leaf surface coloration. Mid-plant leaves, lower surface: Close to 146B to 146C; towards the base, close to 197A; venation, similar to leaf surface coloration. Upper leaves, upper surface: Close to 77B; towards the apex, close to 70B; irregular dark splotches and concentric rings, close to 187A to 187B; venation, close to 70B. Upper leaves, lower surface: More grey than N78C; venation, close to N78C.

Inflorescence description:

*Inflorescence form.*—Terminal flat-topped compact corymb located inside the leaf rosette; about 75 flowers develop per inflorescence.

*Time to flower.*—Plants begin flowering about ten to twelve weeks after planting; plants flower naturally during the spring in Florida.

*Flower longevity.*—Individual flowers last about one day on the plant; flowers persistent.

*Fragrance.*—None detected.

*Inflorescence length.*—About 5.6 cm.

*Inflorescence diameter.*—About 3.5 cm.

*Flower size.*—Length: About 4.4 cm. Diameter: About 7 mm.

*Flower buds.*—Length: About 4 cm. Diameter: About 7 mm. Shape: Narrowly elongate. Color: Close to 92C.

*Petals.*—Quantity per flower: Three in a single whorl. Shape: Oblanceolate. Apex: Acuminate. Base: Truncate. Margin: Entire. Length: About 3.3 cm. Width: About 7 mm. Texture: Smooth, glabrous. Color: When opening, upper surface: Close to 93D; towards the apex, close to 93C; towards the base, close to NN155D. When opening, lower surface: Close to NN155D; towards the apex, close to 93C. Fully opened, upper surface: Close to NN155D; towards the apex, close to 93B. Fully opened, lower surface: Close to NN155D; towards the apex, close to 93C.

*Flower bracts.*—Quantity per flower: One. Shape: Oblanceolate. Length: About 3.5 cm. Width: About 1 cm. Texture: Membraneous. Color: Close to 145C to 145D.

*Sepals.*—Quantity per flower: Three in a single whorl. Shape: Oblanceolate. Apex: Acuminate. Base: Truncate. Margin: Entire. Length: About 2.6 cm. Width:

About 5 mm. Texture: Smooth, glabrous. Color, upper and lower surfaces: Towards the apex, close to 146B; mid-section, close to 146D; towards the base, close to 145D.

*Peduncles.*—Length: About 6 mm. Diameter: About 1 cm. Strength: Strong. Aspect: Typically erect. Texture: Smooth, glabrous. Color: Close to NN155D.

*Pedicels.*—Length: About 9 mm. Diameter: About 3 mm. Strength: Strong. Aspect: Typically erect to somewhat outward and curving upright. Texture: Smooth, glabrous. Color: Close to NN155D.

*Stamens.*—Quantity per flower: Six. Filament length: About 1.7 cm; partially adnate to the petals. Filament color: Close to NN155D. Anther shape: Lanceolate. Anther length: About 5 mm. Anther color: Close to 158C. Pollen amount: Scarce. Pollen color: Close to 158A.

*Pistils.*—Quantity per flower: One. Pistil length: About 3.4 cm. Stigma shape: Oval, elongated. Stigma color: Close to NN155C. Style length: About 2.1 cm. Style color: Close to NN155D. Ovary color: Close to 155D.

*Fruit/seed.*—Fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance and to tolerate wide ranges of light levels.

Disease/pest resistance: Resistance to pathogens and pests common to *Neoregelia* plants has not been observed.

It is claimed:

1. A new and distinct *Neoregelia* plant named 'Sibella' as illustrated and described.

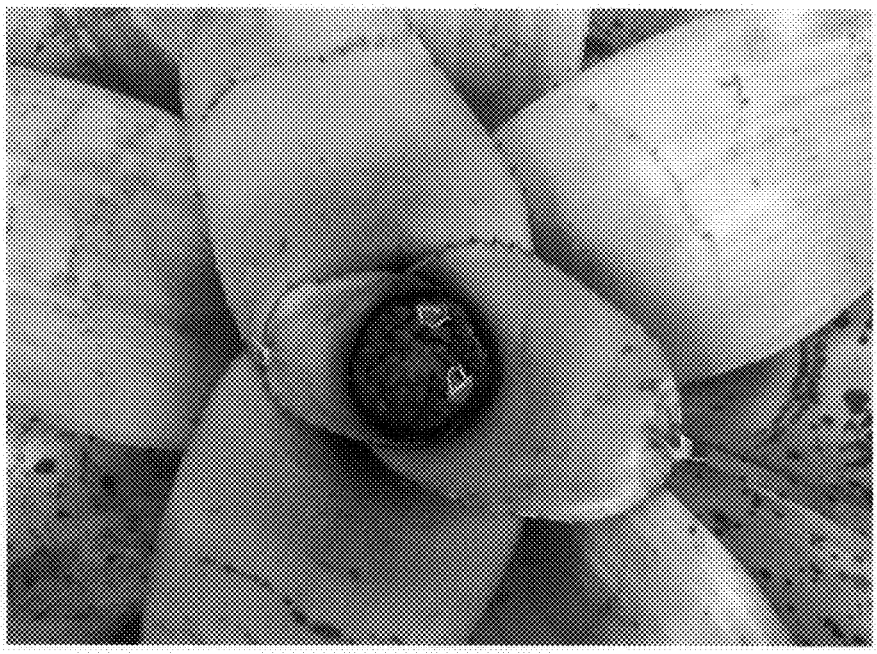
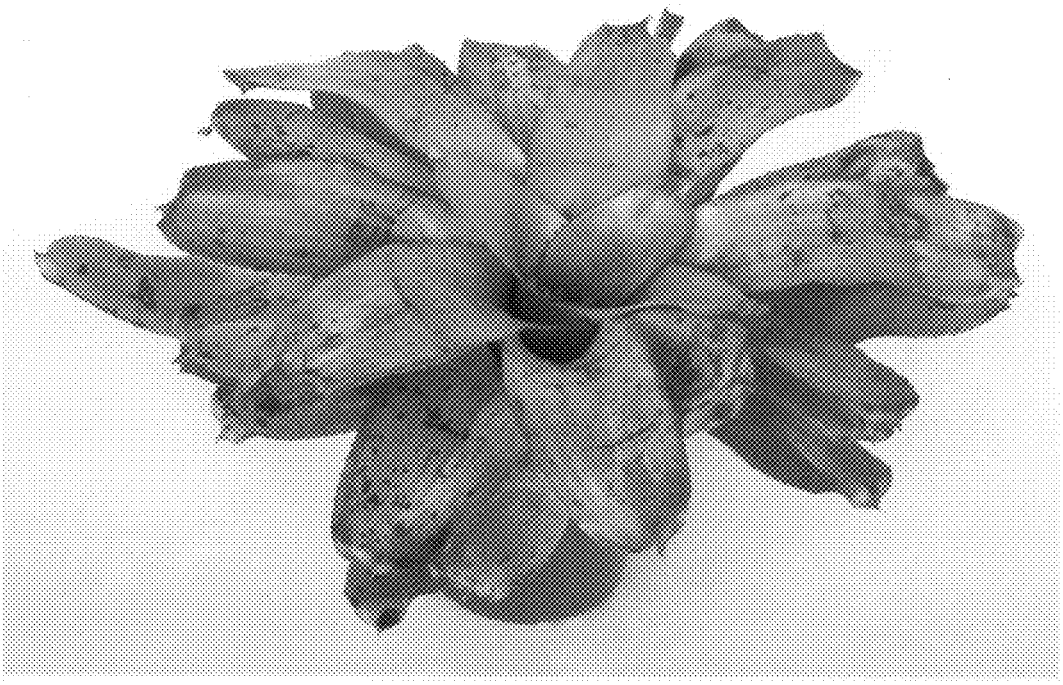

* * * * *